(12) United States Patent
Howlett

(10) Patent No.: US 11,867,159 B2
(45) Date of Patent: Jan. 9, 2024

(54) OSMOTIC ENERGY TRANSFER DEVICES AND METHODS

(71) Applicant: Larry D. Howlett, DeKalb, IL (US)

(72) Inventor: Larry D. Howlett, DeKalb, IL (US)

(*) Notice: Subject to any disclaimer, the term of this patent is extended or adjusted under 35 U.S.C. 154(b) by 201 days.

(21) Appl. No.: 16/216,762

(22) Filed: Dec. 11, 2018

(65) Prior Publication Data

US 2019/0219038 A1 Jul. 18, 2019

Related U.S. Application Data

(60) Provisional application No. 62/708,531, filed on Dec. 11, 2017.

(51) Int. Cl.
- *F03G 7/00* (2006.01)
- *F04B 19/00* (2006.01)
- *A61K 9/00* (2006.01)

(52) U.S. Cl.
CPC ............ *F03G 7/005* (2013.01); *A61K 9/0004* (2013.01); *F04B 19/006* (2013.01)

(58) Field of Classification Search
CPC ...... F03C 1/007; A61K 9/0004; F04B 19/006; F03G 7/005
See application file for complete search history.

(56) References Cited

U.S. PATENT DOCUMENTS

| | | | | |
|---|---|---|---|---|
| 4,522,698 A | * | 6/1985 | Maget | F03G 7/005 204/266 |
| 2007/0021735 A1 | * | 1/2007 | Bhavaraju | A61N 1/306 604/891.1 |
| 2009/0120082 A1 | * | 5/2009 | Lenouvel | F04B 43/02 60/325 |
| 2011/0311372 A1 | * | 12/2011 | Hess | F04B 19/006 417/49 |
| 2016/0025083 A1 | * | 1/2016 | Shin | F04B 19/006 417/48 |

* cited by examiner

*Primary Examiner* — Craig J Price
*Assistant Examiner* — Andrew J Rost
(74) *Attorney, Agent, or Firm* — K&L Gates LLP

(57) ABSTRACT

Osmotic energy transfer systems utilize cyclic electro-chemical stimuli to induce an osmotic gradient and corresponding fluid flows across a semi-permeable membrane. The fluid transfers and osmotic flows are converted into mechanical displacements. By cycling or pulsing the electro-chemical stimuli, fluid transfers across the semi-permeable membrane repeatedly alternatingly change direction over time and correspondingly realizing a cycle of reciprocating mechanical displacements.

9 Claims, 13 Drawing Sheets

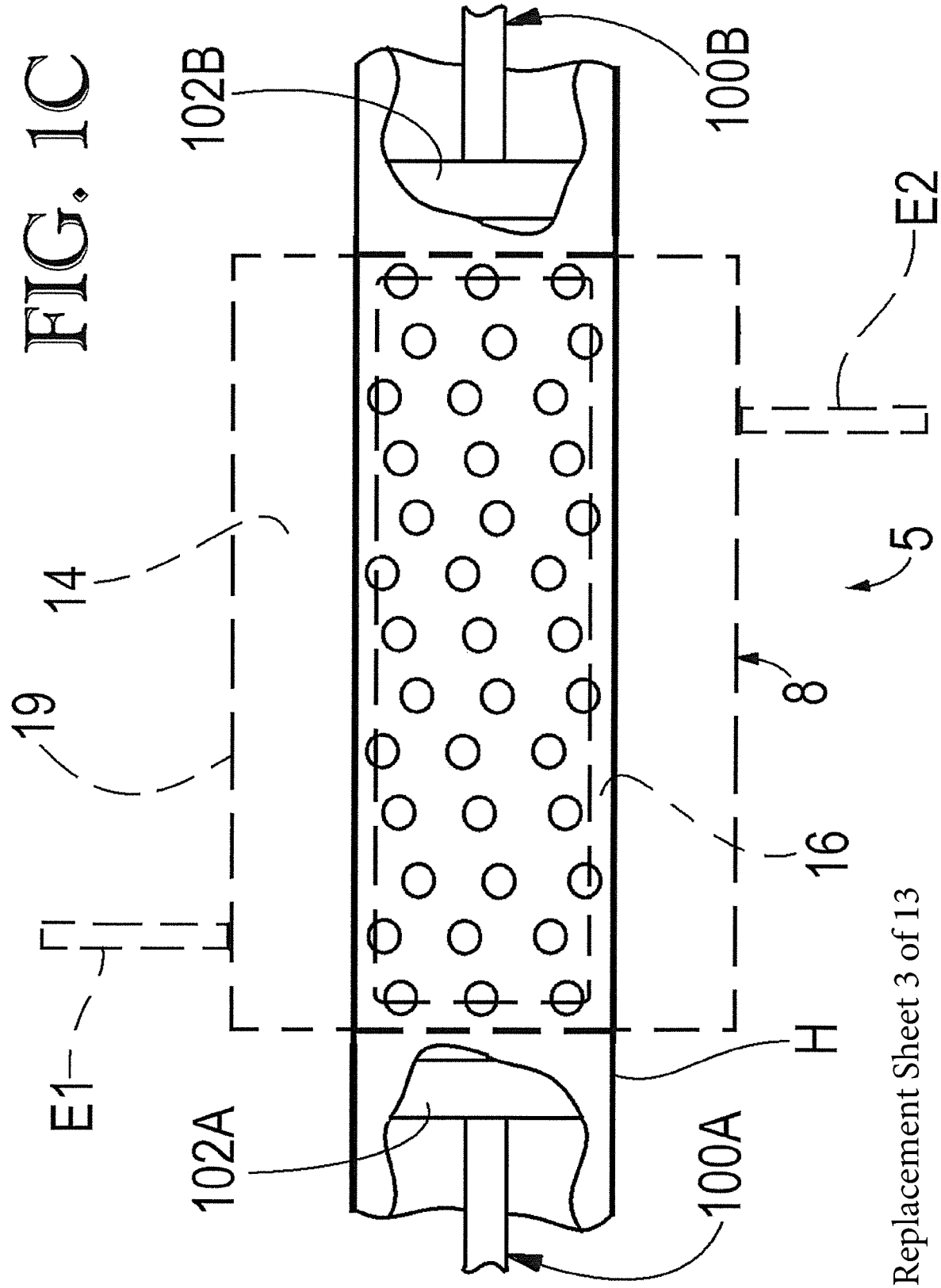

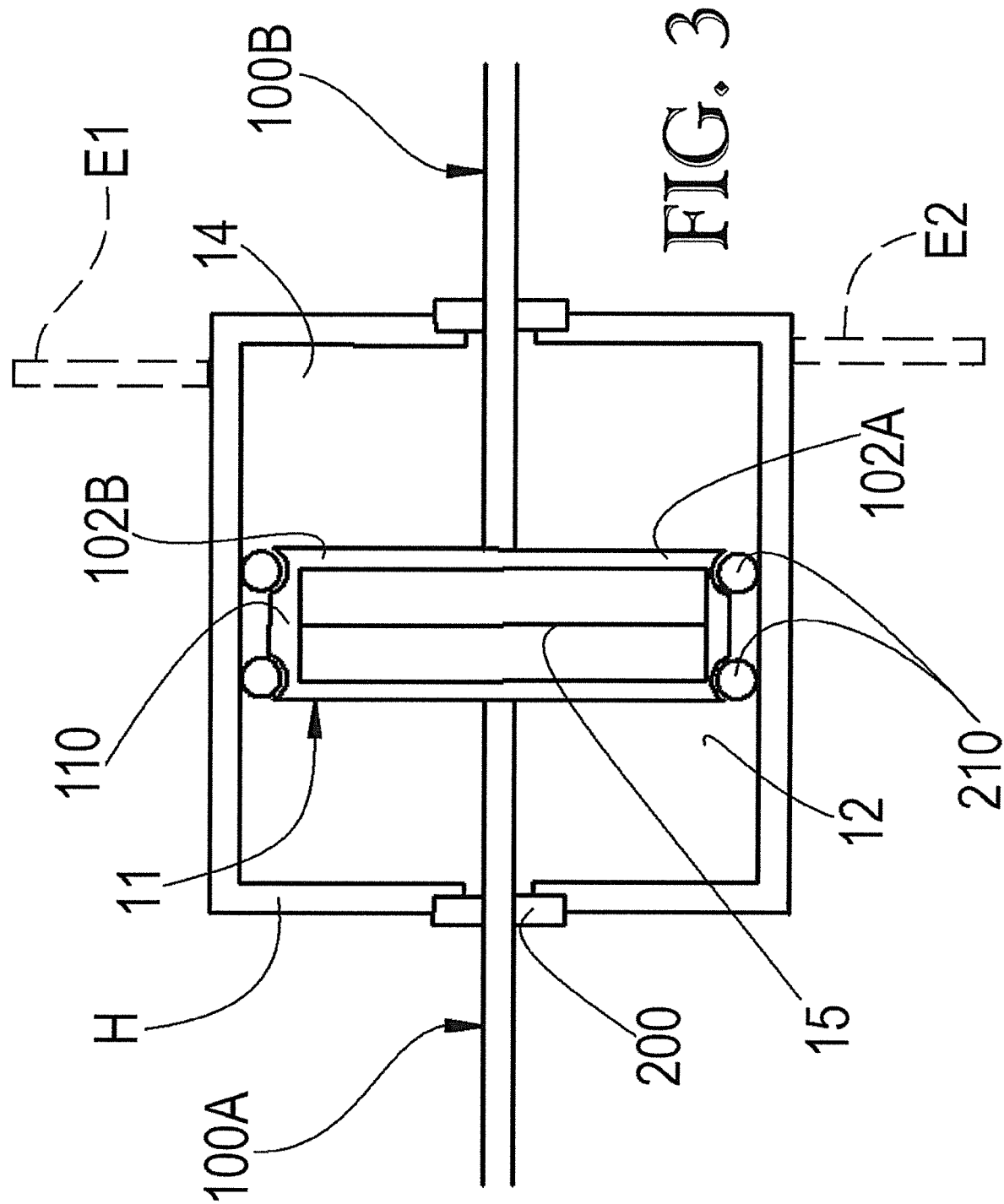

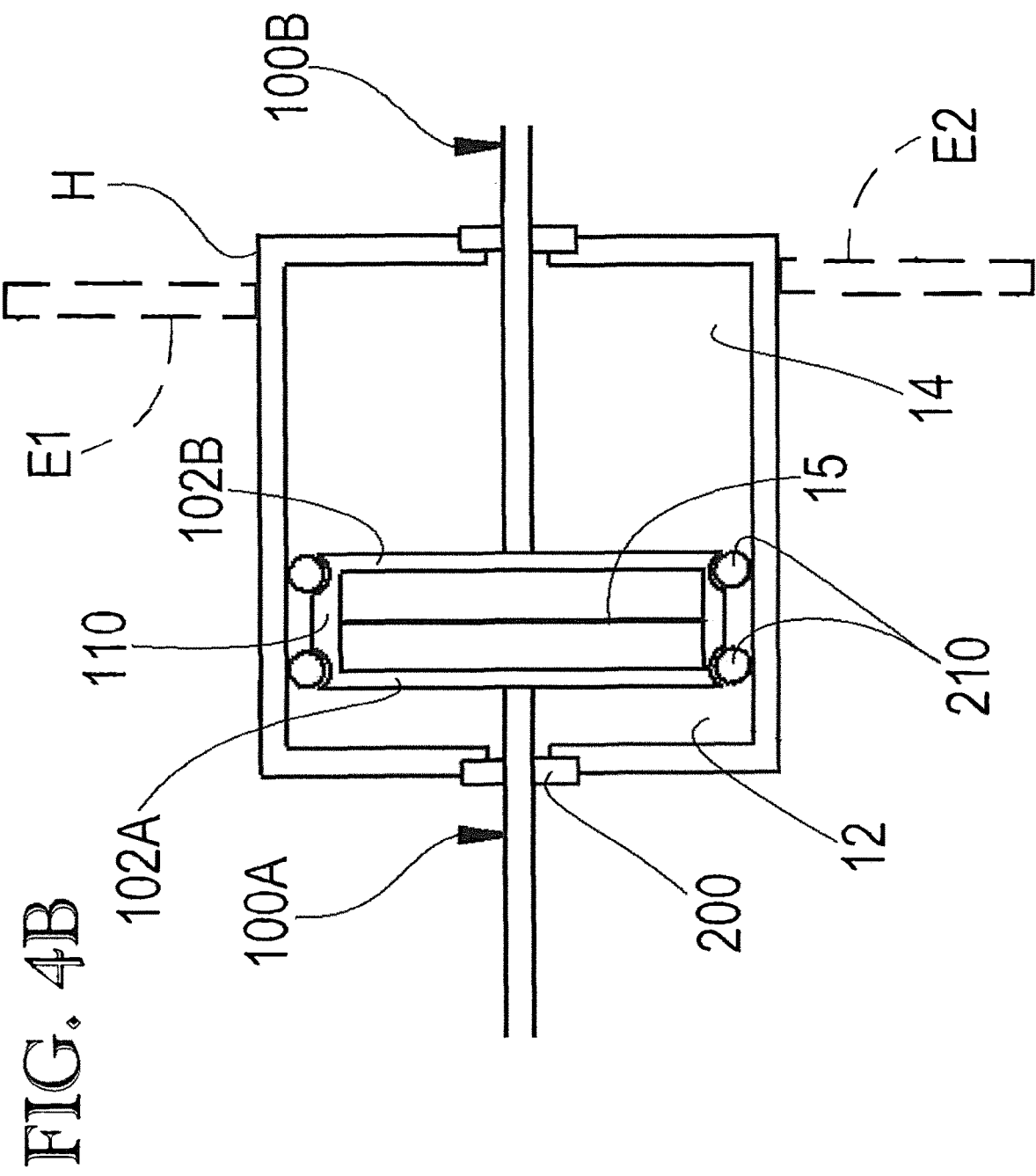

OSMOTIC ENERGY TRANSFER DEVICES AND METHODS

CROSS-REFERENCE TO RELATED APPLICATIONS

This application incorporates by reference and claims the benefit of priority to U.S. Provisional Application No. 62/708,531 filed on Dec. 11, 2017.

BACKGROUND OF THE INVENTION

The present invention is directed generally to devices which transform a first form of energy into a second, different form of energy. Specifically, the invention related to devices which use osmotic flow to perform mechanical work.

Some primarily mechanical systems and devices prove relatively inefficient for performing various work tasks. For example, a device with many movable parts correspondingly has many opportunities for e.g. frictional losses, heat losses, and/or other energy losses, resulting in relatively less efficient conversion of the input energy to the desired work.

In addition, the movable parts of such complex, primarily mechanical devices tend to wear over time, when used. Eventually, such wear will cause the part(s) to fall out of the desired specifications as to e.g. clearances, tolerances, tolerance stack-ups, and others. When part dimensions and characteristics are outside of the desired specifications, the device can operate relatively less efficiently or effectively. In some such instances, various parts or the entire device can fail or break.

Replacing or repairing various parts or subassemblies within primarily mechanical devices can prove cumbersome, burdensome, impractical and/or expensive, depending on the complexity of the device and the various components or parts.

Attempts have been made to reduce the amount of movable mechanical parts in various devices, yet still enjoy the functionality of the predecessor primarily mechanical device. As one example, various osmotic systems have been utilized in various regards to provide e.g. squeeze-pump delivery devices to deliver pharmaceutical or medicinal agents to recipients.

However, such squeeze-pump delivery devices deliver various liquids at relatively low flow and precisely-controlled rates. They are predominately configured for a limited use-time which corresponds to the delivery time of such pharmaceutical or medicinal agent.

It might therefore prove beneficial to provide osmotic based energy conversion or transfer devices which can perform sustained work for relatively long periods of time.

SUMMARY

Osmotic energy transfer systems of the invention utilize cyclic electro-chemical stimuli to induce osmotic flow across a permeable membrane. The fluid transfers are converted into mechanical displacements. By cycling or pulsing the electro-chemical stimuli, fluid transfers across the semi-permeable membrane repeatedly alternatingly change direction over time. Correspondingly, by providing cyclic or pulsed electric stimulus, the device provides reciprocating mechanical movement which can do any of a variety of suitable work.

In a first family of embodiments, the invention comprehends a method of transferring energy utilizing osmosis, the method comprising: (a) providing an osmotic system having: (i) a working body which is deformable and which defines an enclosure having a cavity; (ii) a semi-permeable membrane which separates the working body cavity into first and second compartments; (iii) a solvent fluid which occupies the first and second compartments, is transferable therebetween through the semi-permeable membrane, and has solute contained therein; (iv) an actuatable member interfacing with the working body such that deformations of the working body correspond to a positional translation of the actuatable member; (b) subjecting the working body to an electric field; (c) influencing an osmotic event in response to the electric field by: (i) establishing an osmotic gradient across the semi-permeable membrane by changing the concentration of readily available solute within the solvent in at least one of the first and second compartments; (ii) transferring solvent fluid from the compartment with the relatively lesser concentration of solute, across the semi-permeable membrane, into the compartment with the relatively greater concentration of solute; (d) deforming the working body and correspondingly positionally translating the actuatable member from a first position to a second position; (e) attenuating the intensity of the electric field, again deforming the working body, and correspondingly positionally translating the actuatable member from the second position to the first position.

In some embodiments, the method further includes the step of repeatedly subjecting the working body to an electric field and attenuating the intensity of the electric field.

In some embodiments, the actuatable member translates along a generally linear travel path.

In some embodiments the method includes the step of converting the translating movement of the actuatable member into a rotational movement.

In some embodiments, the method includes the step of providing a piston which lies between the working body and the actuatable member.

In some embodiments, the method includes the step of providing an electrolyte solution as the solvent and solute.

In some embodiments, the method includes deforming the working body by generally axially stretching the working body.

In some embodiments, the method includes deforming the working body by generally axially compressing the working body.

In a second family of embodiments, the invention comprehends a method of converting energy of an osmotic system into a different form of energy, the method comprising: (a) providing a working body which defines an enclosure having a fluid filled cavity therein and having a semi-permeable membrane housed in the cavity which generally divides the cavity into first and second opposing chambers; (b) introducing an electric field to the working body and correspondingly driving an osmotic response across the semi-permeable membrane in a first direction of fluid transfer and converting forces associated with such fluid transfer into mechanical movement of an actuatable member in a corresponding first direction of movement; (c) manipulating the electric field so as to drive an osmotic response across the semi-permeable membrane in a second, opposite, direction of fluid transfer and converting forces associated with such fluid transfer into mechanical movement of the actuatable member in a corresponding second, opposite, direction of movement; (d) repeatedly manipulating the electric field such that the actuatable member cycles between first and second positions which respectively correspond to the first and second directions of movement.

In some embodiments, the method includes establishing an electric field by providing a direct current (DC) signal.

In some embodiments, the electrical signal is an alternating current (AC) signal.

In some embodiments, the first and second positions correspond to the maximum distance traveled by the actuatable member in the first and second directions, respectively.

In a third family of embodiments, the invention comprehends an energy transfer device comprising: (a) a fluid filled working body which is osmotically responsive to an electrical signal and which defines first and second chambers on opposing sides of a semi-permeable membrane; (b) an actuatable member movable between first and second positions, the actuatable member interfacing with, and driven by, the working body in response to the osmotic activity of the working body (c) an electrical power source in electrical communication with the working body; and (d) an electrical controller in electrical communication with the electrical power source and the working body, which controls an electrical signal realized at the working body; whereby the electrical controller modifies the electrical signal realized at the working body over a given time, such that changes to the signal over time correspond to changes in the direction of osmotic activity across the semi-permeable membrane over time and the direction of movement of the actuatable member over time.

In some embodiments, the electrical signal is a direct current (DC) signal.

In some embodiments, the electrical signal is an alternating current (AC) signal.

BRIEF DESCRIPTION OF THE DRAWINGS

FIG. 1C shows a top, plan, view of another variant of the osmotic energy transfer device of FIG. 1A with the actuatable member(s) in a first, relatively inward, position, with partial cutaway sections at each end.

FIG. 3 shows a cross sectional view of a second embodiment of osmotic energy transfer devices of the invention with the actuatable member(s) in a resting state.

FIG. 4B shows cross sectional view of the osmotic energy transfer device of FIG. 3 with the working body in a second osmotically urged position.

Figure 1A:
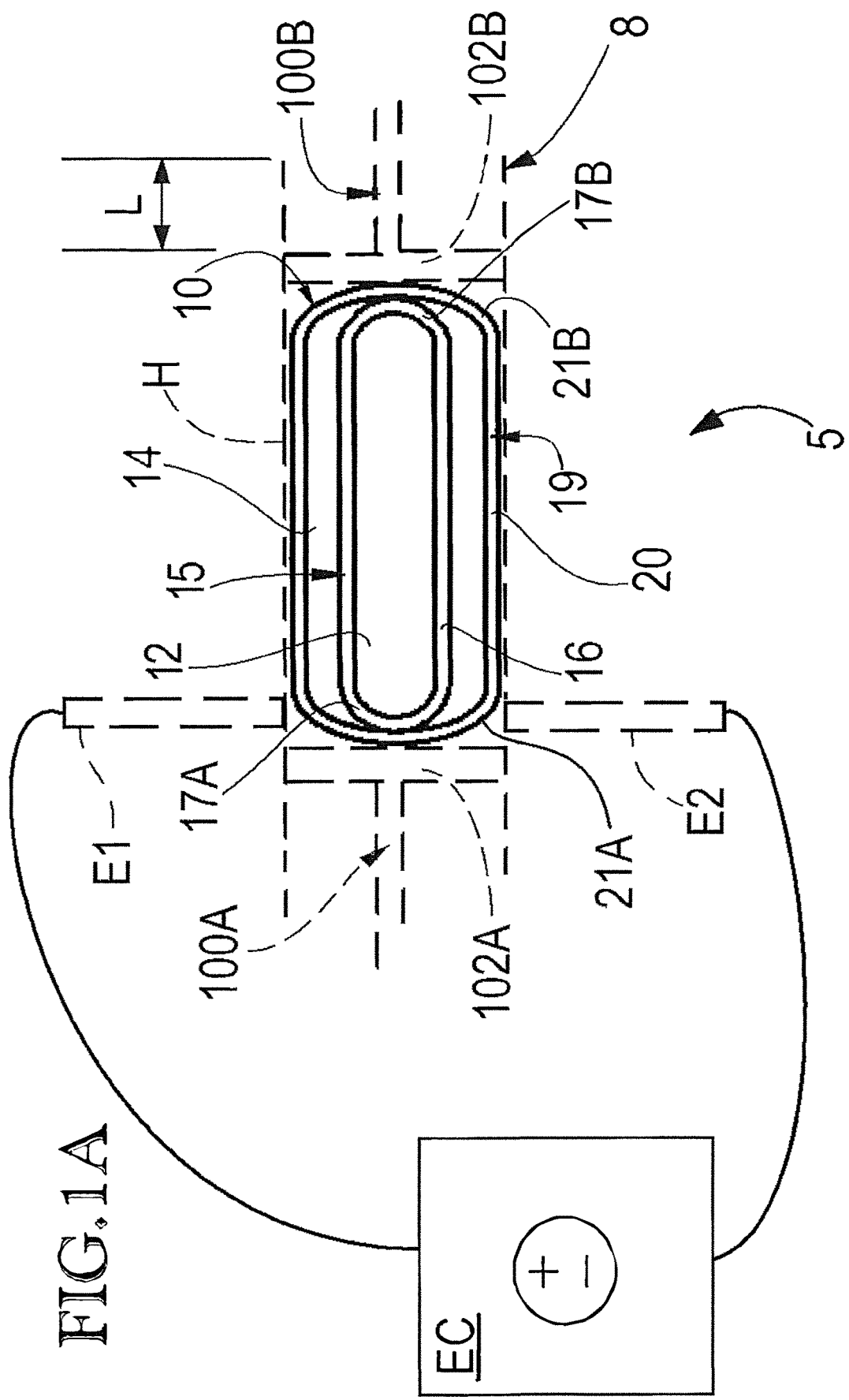
FIG. 1A shows a top, plan, view of a first embodiment of osmotic energy transfer devices of the invention with the actuatable member(s) in a first, relatively inward, position.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DETAILED DESCRIPTION OF THE INVENTION

Referring first to all the FIGURES, in general, osmotic energy transfer systems 5 are cyclic electrochemical osmotic pump which exploits osmotic flow to perform mechanical work. In other words, osmotic energy transfer systems 5 of the invention are electrochemical devices which utilize electrical signals, chargers, and/or other corresponding electrical forces to control or otherwise influence various chemical tendencies and interactions within an osmotic device 8 of the system. The controlled or influenced chemical tendencies, in turn, alter a pressure gradient across a semi-permeable membrane 15.

The osmotic flow is used to cause movement of a solvent through an osmotic membrane and to correspondingly cause movement of an enclosing outer structure. The movement of the enclosing outer structure is captured as mechanical work. Preferably, the mechanical work is realized by e.g. actuating a linear actuator, pushing a piston or rod, or other suitable work based on the intended end use environment and implementation. In other words, the invention uses electrical stimuli to influence chemical interactions and correspondingly osmotic flow, which are in turn converted to mechanical displacement(s).

In general system 5 includes an electrical controller "EC" (FIGS. 1A, 1B, 1C), housing structure "H", and osmotic device 8. Housing "H" is an elongate, generally rigid structure having a void defined within its perimeter wall(s). The void space of housing "H" houses at least part of osmotic device 8 therein.

Osmotic device 8 includes working body 10, at least one actuatable member 100A, 100B, and at least one electrode "E1", "E2". As schematically illustrated, each of electrodes "E1" and "E2" is electrically connected to portions of the osmotic device 8 such as membrane 19 or otherwise. In addition, each electrode "E1", "E2." is electrically connected by way of, for example, conductors to the electrical controller "EC." Although not illustrated as such in the schematic-style FIGURES, each electrode "E1" and "E2" further includes various accessories to ensure proper operation such as, for example, various insulating coverings, insulated junction fixtures, dielectric unions, and/or others are required for suitable functionality based on the intended use.

Electrical controller includes a power supply, various other electronic devices such as various circuits, function generators, user inputs, and/or other controls. The electrical controller "EC" preferably provides direct current (DC) to the system 5, although alternating current (AC) can also be used as desired. Those skilled in the art are well aware of suitable electrical controllers and corresponding circuitry therein to provide adequate DC or AC electrical signal(s) and, as necessary, AC waveforms, to arrive at the intended functionality of the device.

Working body 10 defines an inner chamber 12, outer chamber 14, and various membranes or containment vessels e.g. semi-permeable membrane 15 and outer membrane 19. Namely, inner chamber 12 is generally defined by the space within the inner surface of membrane 15 and the outer chamber 14 is generally defined as the space between the outer surface of membrane 15 and the inner surface of membrane 19.

Each of chambers 12 and 14 is fluid filled, preferably solvent fluid filled. At least one of the chambers 12, 14 further includes various e.g. solutes, particles, compounds, ions, and/or other substances therein. The particular chemical reactability, solubility, and/or other availability of such solutes, particles, compounds, ions, and/or other substances, is influenced by their exposure to electric charge, current, field, or other electrical or magnetic stimulus. Correspondingly, by influencing and modifying the chemical reactability, solubility, and/or other availability of such solutes, particles, compounds, ions, and/or other substances, various characteristics of the solvent or overall solution are likewise influenced or modified.

In particular, chambers 12 and 14 communicate with and are generally separated from each other through semi-permeable membrane 15. Semi-permeable membrane 15 is exemplarily described herein as being selected for its ability to pass water therethrough, whilst generally blocking the passage of impurities. However, it is fully understood that membrane 15 is selectively permeable and in some embodiments, allows only certain molecules, compounds, or ions to pass therethrough, in addition to water.

In other words, semi-permeable membrane 15 provides selective passage of substances between chambers 12 and 14. Those skilled in the art are well aware of suitable membranes and corresponding methods of manufactures to provide the desired end use characteristics of the semi-permeable membrane 15.

Membrane 15 includes a main body portion 16 and first and second end portions 17A, 17B. The main body portion is generally tubular and elongate and spans between the first and second end portions 17A, 17B.

Each of first and second end portions 17A, 17B generally defines an end closure structure of the membrane 15. Accordingly, end portion 17A is attached to a first end opening of main body portion 16 and generally, seals closed a first end of membrane 15 while being selectively permeably. Correspondingly, end portion 17B is attached to a second end opening of main body portion 16 and generally, and preferably selectively permeably, seals closed a second end of membrane 15.

The overall assemblage of membrane 15 is adapted and configured to flex, stretch, expand, elongate, contract, deform, and/or otherwise distort based on e.g. relative osmotic flow through the membrane 15 wall. In other words, the physical configuration and dimensions of membrane 15 vary over time depending on the particular relative pressures within the first and second chambers 12, 14 at such particular time.

Preferably, membrane 15 distorts in a predominately lengthwise, longitudinal, or axial direction. Such physical limitation on the expansion and/or contraction of membrane 15 is controlled in any of a variety of suitable ways.

Outer membrane 19 is in many ways an analogue of membrane 15. However, unlike semi-permeable membrane 15, outer membrane 19 is generally impermeable and adapted and configured to not allow the solvent fluid to pass therethrough. Membrane 19 includes a main body portion 20 and first and second end portions 21A, 21B. The main body portion 20 is generally tubular and elongate and spans between the first and second end portions 21A, 21B.

Each of first and second end portions 21A, 21B generally defines an end closure structure of the membrane 19. Accordingly, end portion 21A is attached to a first end opening of main body portion 19 and generally seals closed a first end of membrane 19. Correspondingly, end portion 21B is attached to a second end opening of main body portion 19 and generally seals closed a second end of membrane 19.

Membrane 19 is adapted and configured to flex, stretch, expand, elongate, contract, deform, and/or otherwise distort based on e.g. relative pressures it is exposed to. In other words, the physical configuration and dimensions of membrane 19 vary over time depending on the particular relative pressures within the first and second chambers 12, 14 at such particular time. In general, membrane 19 expands, contracts, and/or otherwise deforms based on the volume of chamber 14 and the particular shape and configuration of semi-permeable membrane 15 at a given time.

Figure 2A:
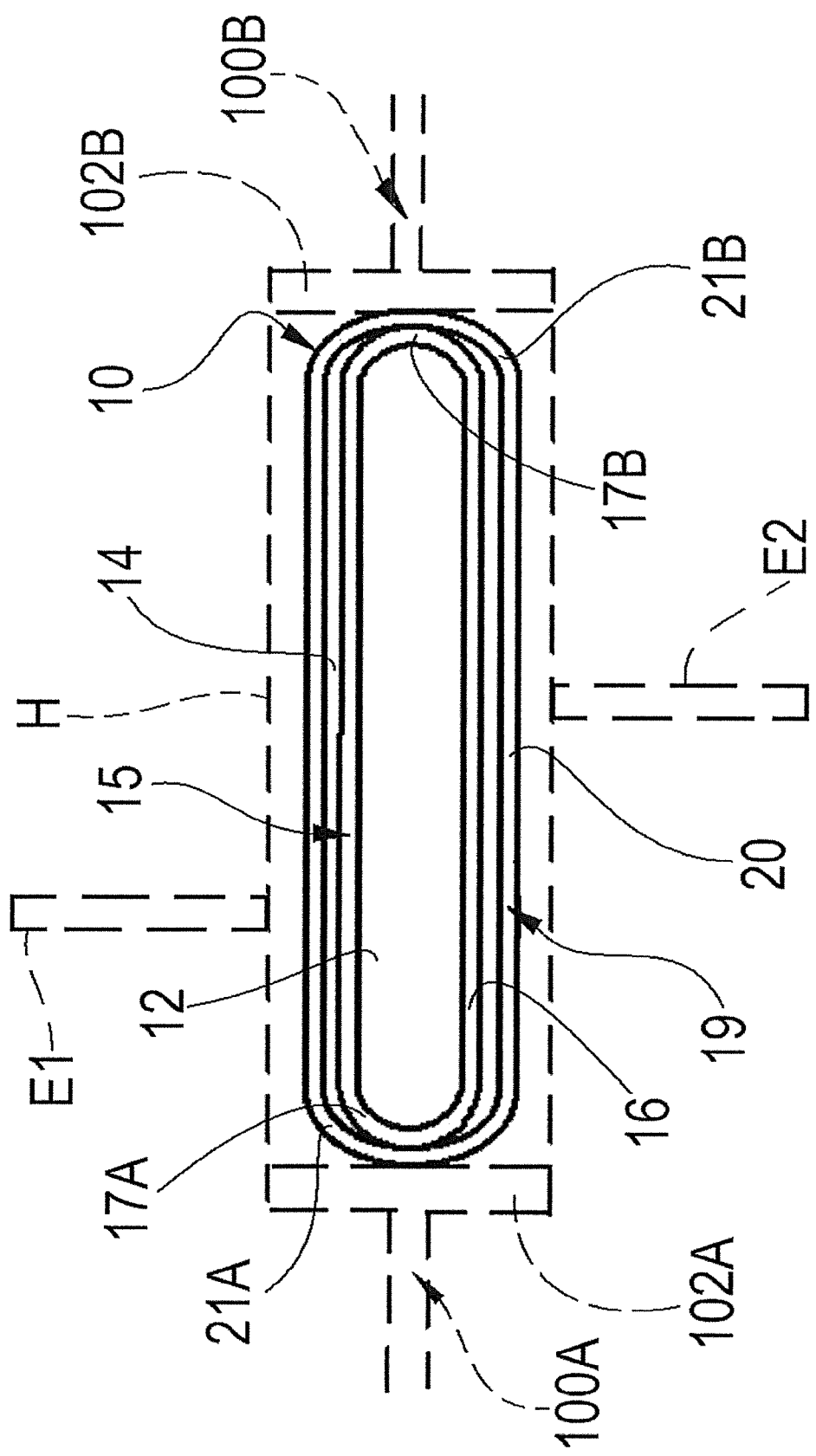
FIG. 2A shows a top, plan, view of the osmotic energy transfer device of FIG. 1A with the actuatable member(s) in a second, relatively outward, position.

In some embodiments, the physical limitations which restrict radial expansion are imposed and provided for by non-membrane structural materials, be it the housing "H" itself or an ancillary structure. FIGS. 1A and 2A illustrate embodiments in which housing "H" restricts or controls radial expansion of the membranes. FIG. 2A in particular illustrates generally the maximum expanded diameter that is realized by chambers 12 and 14 and correspondingly the maximum radial expansion of membranes 15 and 19.

In other words, the rigidity, resiliency, and/or other structural integrity of housing "H" mechanically prevents membranes 15 and 19 from radially expanding beyond the inner surface of the housing "H". Accordingly, any urge of membranes 15 and 19 to expand are translated and limited to generally axial or longitudinal elongation or expansion.

In other embodiments, the physical limitations which restrict radial expansion are imposed and provided for by non-membrane structural materials and non-housing "H" materials, whereby the radial expansion restriction mechanism is an ancillary or auxiliary structure. Such containment structures can restrict radial expansion of semi-permeable membrane 15, outer membrane 19, or both, as desired.

Figure 1B:
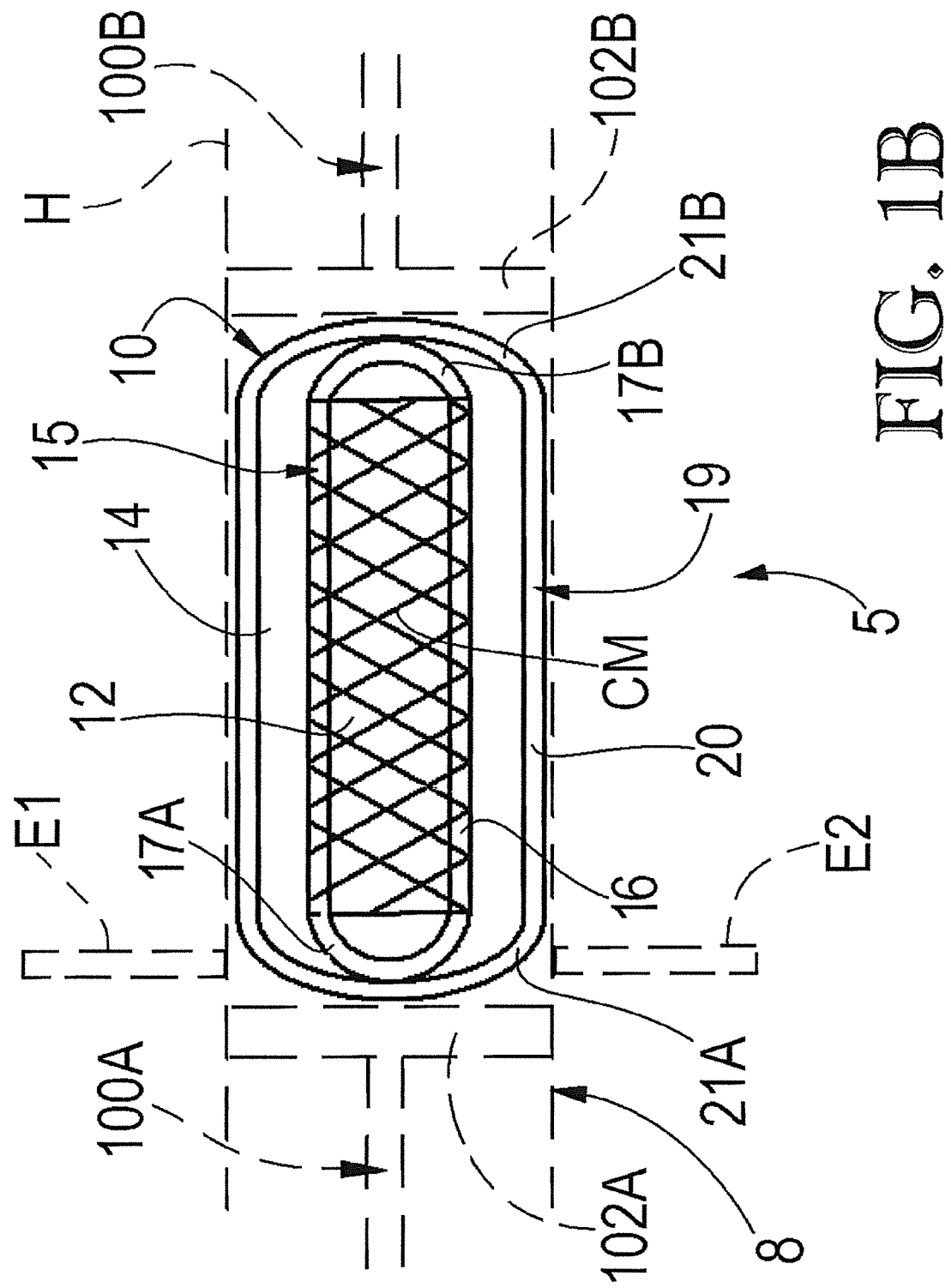
FIG. 1B shows a top, plan, view of a variant of the osmotic energy transfer device of FIG. 1A with the actuatable member(s) in a first, relatively inward, position.
Figure 2B:
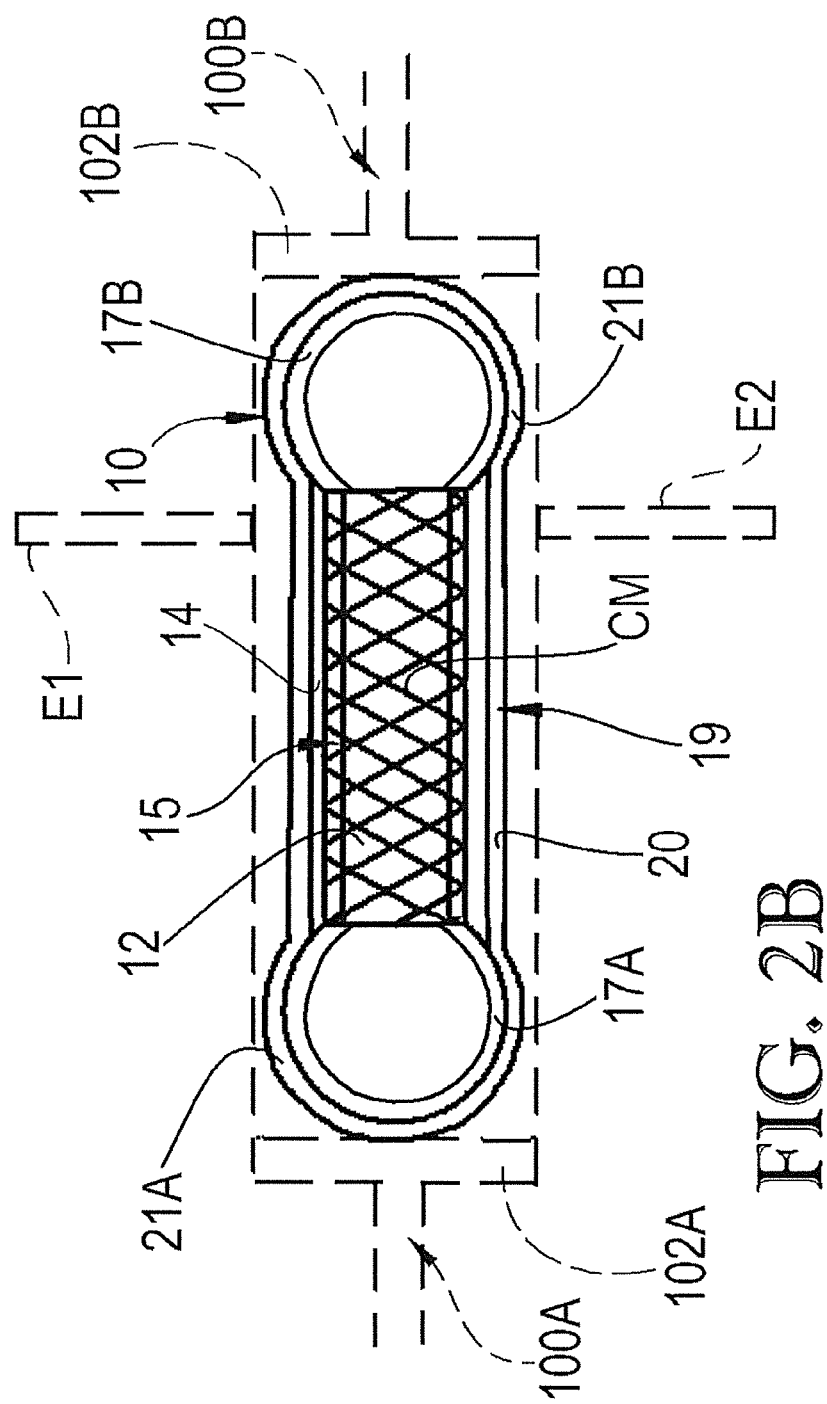
FIG. 2B shows a top, plan, view of the osmotic energy transfer device of FIG. 1B with the actuatable member(s) in a second, relatively outward, position.

FIGS. 1B and 2B, illustrate embodiments which include containment member "CM" which restricts the radial expansion of only the semi-permeable membrane 15. Containment member "CM" is an elongate, rigid, hollow member which circumferentially surrounds a portion of semi-permeable membrane 15.

As illustrated, containment member "CM" is preferably highly permeable, illustrated as an e.g. wire mesh, thereby adequately preserving the integrity of the interface between chamber 14 and the semi-permeable membrane 15. As shown in FIG. 2B, when the diameter of containment member "CM" is generally lesser in magnitude that the diameter of housing "H", a major portion of the length of semi-permeable membrane 15 is limited to generally only axial or longitudinal expansion. However, the ends of membrane 15 will expand in a bulbous or spherical fashion, whereby the end portions of membrane 15 again realize a radial expansion limitation defined by the inner surface of housing "H".

Figure 2C:
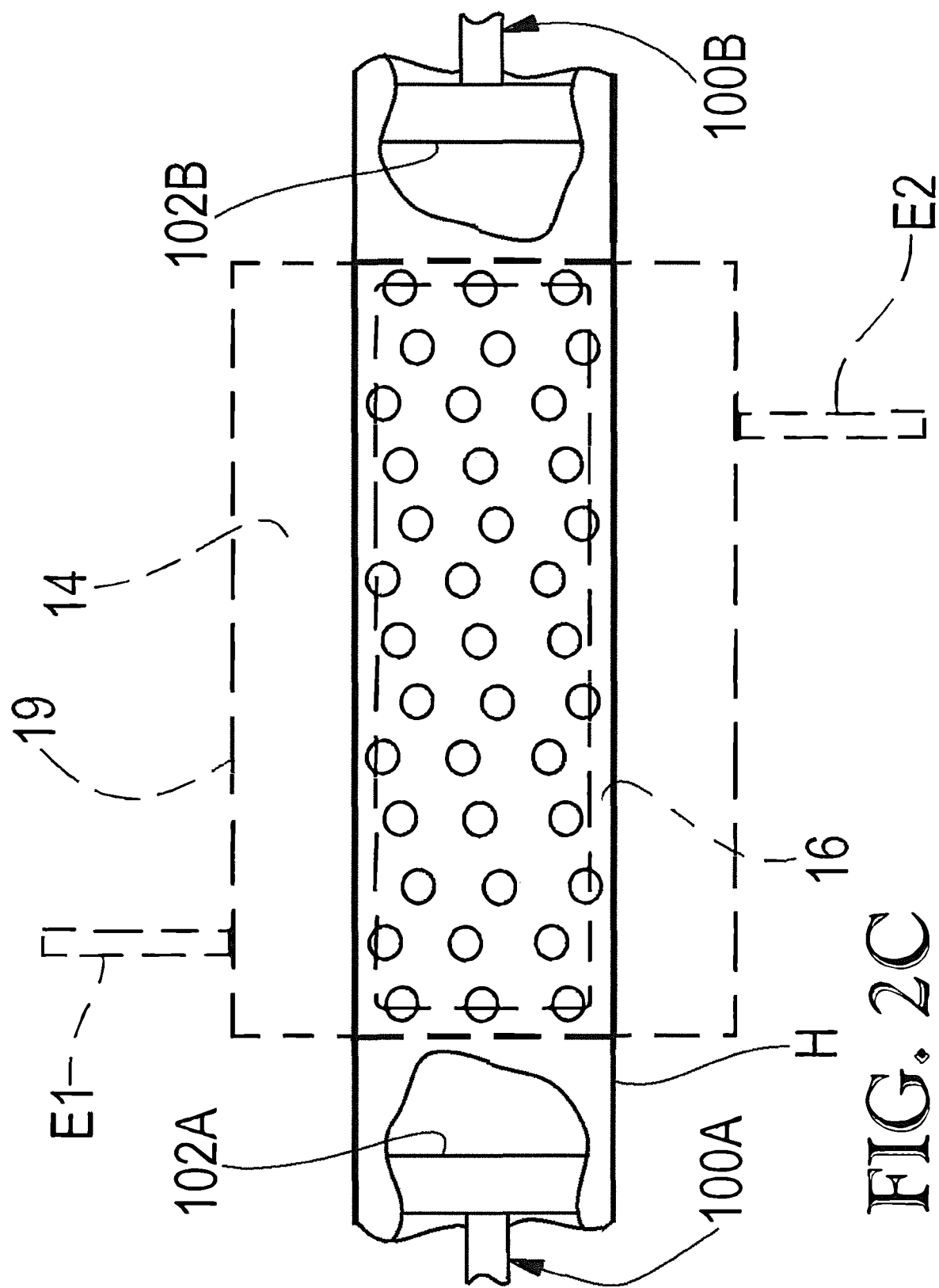
FIG. 2C shows a top, plan, view of the osmotic energy transfer device of FIG. 1C with the actuatable member(s) in a second, relatively outward, position.
Figure 4A:
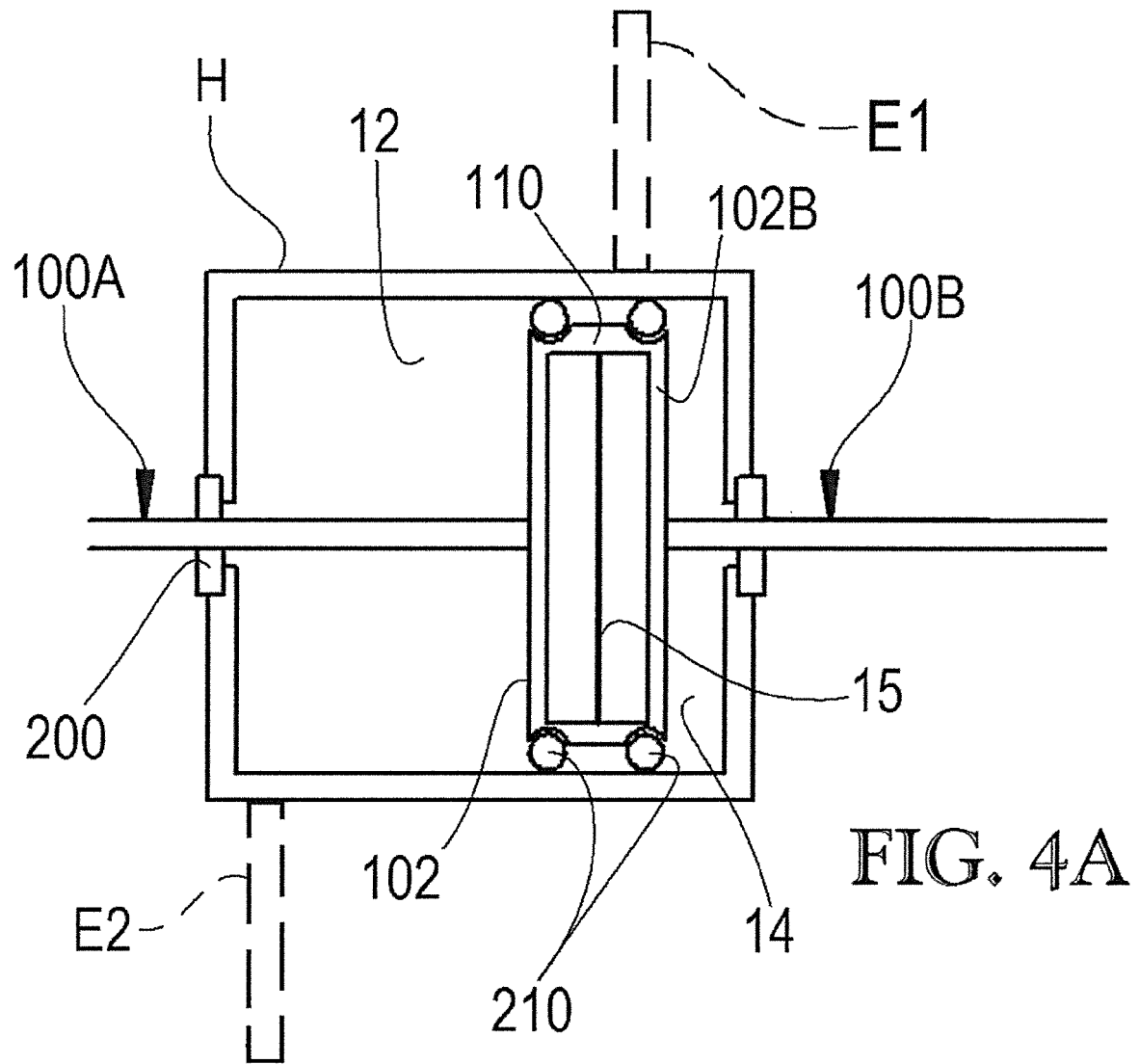
FIG. 4A shows cross sectional view of the osmotic energy transfer device of FIG. 3 with the working body in a first osmotically urged position.

Referring now to FIGS. 1C and 2C, in some embodiments, the physical limitations which restrict radial expansion are imposed and provided for by a containment member "C" that is generally integral with housing "H". In such embodiments, the outer membrane 19 can actually circumferentially surround the containment member "CM".

In embodiments where the outer membrane 19 lies outside the containment member "CM", the containment member "CM" again defines a highly porous wall structure, enabling the contents of chamber 14 to suitably interface and interact with semi-permeable membrane 15. In addition, in such embodiments, outer membrane 19 is suitably sealed to the outer surface of containment member "CM", whereby the contents of outer chamber 14 are adequately maintained within the osmotic device 8.

In yet other, non-illustrated, embodiments, the membrane 15 itself controls both the passage of material(s) therethrough and the physical expansion properties of the membrane. As one example, in some embodiments, main body portion 16 includes a series of annular ring segments which have a relatively greater cross-sectional area than the non-annular ring segments.

The relatively thicker annular ring portions generally restrict radial expansion of the outermost portions of main body 16 while permitting axial expansion. In other words, when the relative pressure within chamber 12 is greater than that within chamber 14, and as the pressure within chamber 12 increases over time, adjacent annular ring segments drift relatively further from each other whilst the thinner, non-ring segments stretch and expand.

Actuatable members 100A, 100B interface and cooperate with the membranes 15, 19 and are adapted and configured to translate e.g. the axial or longitudinal expansion of semi-permeable membrane 15 into mechanical work. Actuatable member 100A includes a piston portion 102A and an elongate connecting rod portion. Likewise, actuatable member 100B includes a corresponding piston portion 102B and an elongate connecting rod portion.

Each of piston 102A and 102B provides the interface structure between the respective actuatable member 100A, 100B and the membranes 15, 19. Each piston 102A, 102B is slidingly housed in housing "H", adjacent the end walls of membranes 15 and 19. In other words, the sizes, configurations, and dimensions of the pistons 102A, 102B correspond to those of the opening within housing "H", whereby the pistons 102A, 102B suitably freely slide within the housing "H" without e.g. binding. This enables the pistons 102A, 102B to reciprocatably travel within the housing "H" during use.

Regarding the connecting rod portions of the actuatable members 100A, 100B, a first end of each of the elongate connecting rod portions is connected to the respective piston 102A, 102B. In other words, the connecting rods extend axially outwardly from the pistons. The second ends of the connecting rods are attached to any of a variety of supplementary devices, depending on the intended end use.

Accordingly, in the complete assemblages of osmotic energy transfer systems 5, such as those shown in FIGS. 1A, 1B, 1C, 2A, 2B, and 2C, in response to exposure to e.g. the electrical signal or stimulus, dynamic characteristics such as relative pressures of the chambers 12, 14 and thus the pressure differential of chamber 12 with respect to chamber 14 varies over time.

In response to this variation, the membranes 15, 19, flex, stretch, expand, elongate, contract, deform, and/or otherwise distort, and push outwardly against the actuatable members 100A, 100B, urging them axially outwardly away from each other. In embodiments which include only one actuatable member, the flexing and deformation of the membranes 15, 19 force the single actuatable member to axially travel, outwardly away from the remainder of the device.

In other words, osmotic energy transfer systems 5 convert energy associated with cyclically inducing osmotic flow between cavities into corresponding generally linear reciprocation of the actuatable members 100A, 100B. During reciprocation, the distance traveled by the actuatable members 100A, 100B corresponds to the magnitude of the change in the length dimension(s) of membranes 15, 19 while the flex, contract, and deform in response to osmotic influences. The distance traveled by the actuatable members 100A, 100B, or stroke length, is illustrated in FIG. 1A as length "L".

The generally linear reciprocation of actuatable members 102A, 102B is thence used to any of a variety of suitable work functions, which lend themselves to generally linear reciprocating input forces. Non-limiting examples include, actuating or otherwise controlling valves, rotating flywheels, generators, pumps, transmission input shafts, and/or others, on micro, nano, and macro scales, as desired.

Referring now to FIGS. 3, 4A, 48, and 5, in some embodiment, the semi-permeable membrane 15 is relatively rigid or non-flexible or non-deformable. In such embodiments, the varying of relative volumes of chambers 12 and 14 comes, not by way of stretching membrane 15 and contracting membrane 19, but rather by way of advancing or regressing the entire membrane 15 within the osmotic device 8 in response to the changing osmotic pressure within the device.

In such embodiments, working body 11 is a generally annular structure having a generally cylindrical outer wall which generally defines its outer perimeter. The semi-permeable membrane 15 spans across the interior of the working body, generally defining a web across the void of the inner circumferential surface of the wall. Such embodiments are typically devoid of an outer membrane 19.

Figure 5:
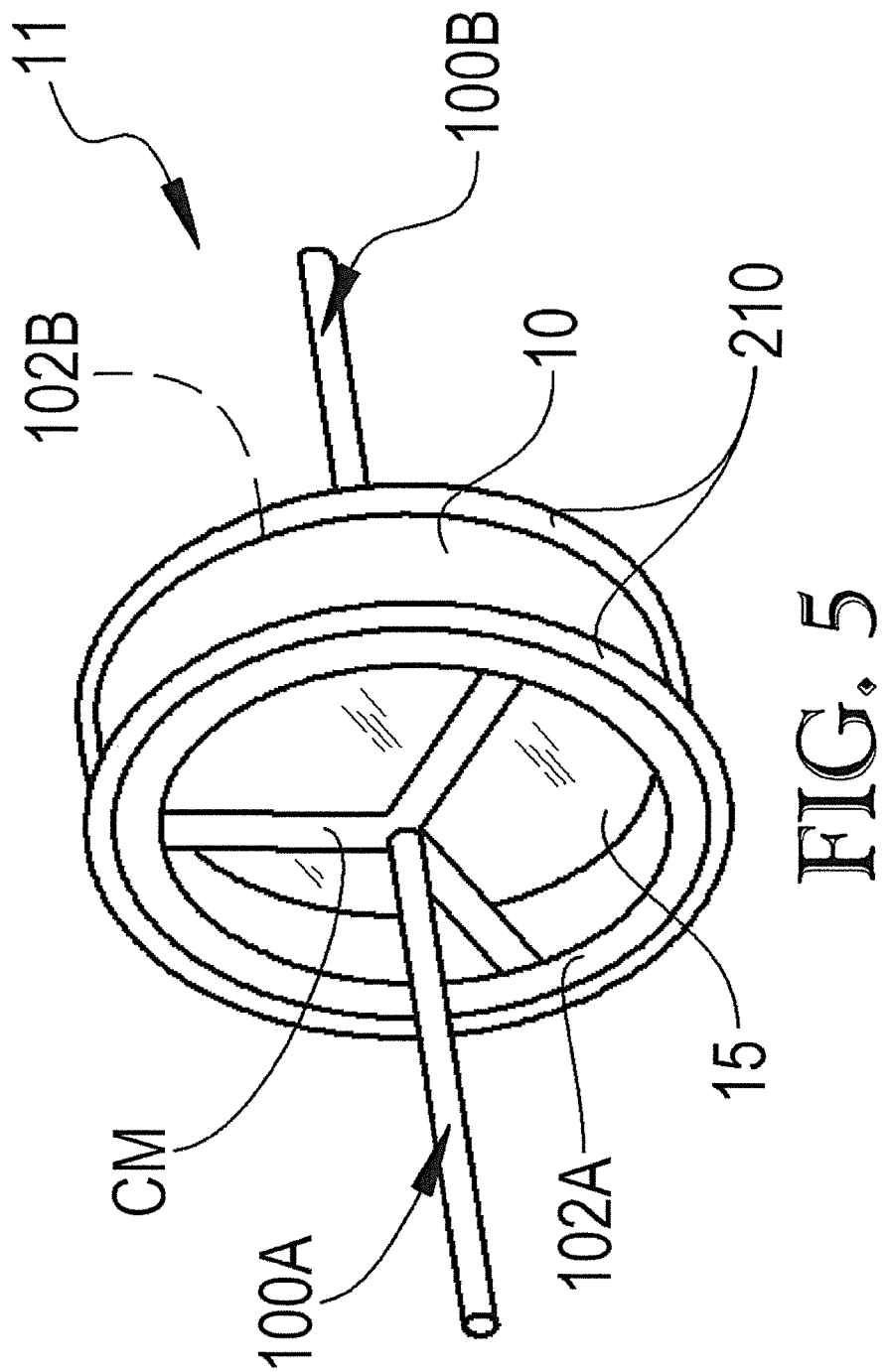
FIG. 5 shows a pictorial view of the working body of FIG. 3.

Referring now to FIG. 5, one or more connecting members "CM" extend radially inwardly from the inner circumferential surface of the working body 11 sidewall, toward the central portion thereof. The overall working body 11 is sized and configured to correspond with the opening dimensions of housing "H" so that the working body fits snugly yet slidably within the housing "H".

The actuatable members 100A, 100B are attached to the connecting members, proximate the central axis of working body 11. The two actuatable members 100A, 100B are generally coaxially aligned with each other, yet extend axially away from the working body 11 and thus also away from each other.

The outer circumferential surface of working body 11 further includes e.g. one or more circumferential seals e.g. rings 210. Rings 210 define the outermost perimeter of the working body 11 and thus the outermost portion of the separation structure between the cavities 12 and 14.

Rings 210 are sized, adapted, and configured, to enable generally freely sliding communication between the working body 11 and housing "H" whilst sufficiently providing a seal between the body 11 and housing "H". Such sealing properties provide that majority of fluid transfer between cavities 12 and 14 must be by way of traversing through the semi-permeable membrane 15. Accordingly, when an osmotic gradient is established across the membrane 15, the solvent will pass through the membrane to mitigate the difference in solute concentration between the two cavities 12, 14.

The system seeks equilibrium by the solvent crossing the membrane, from the low-solute concentration (source) cavity to the high-solute concentration (target) cavity, increasing the pressure within the target cavity and in turn urging working body 11 axially through the housing "H". Thence, the volume of the target cavity increases and the volume of the source cavity decreases until the hydrostatic pressure, the forces on opposing sides of the membrane are generally equal, and thus the solvent flow ceases.

In other words, at any given time, the axial position of working body 11 within housing "H" corresponds to the relative concentration of chemically available solute within the cavities 12, 14, the respective volumes of cavities 12, 14, and the osmotic condition of the device, at that particular time. Changes in various ones of these parameters correspondingly urge change(s) in the axial position of the working body. Since the solvent is preferably a generally incompressible liquid, as the system seeks osmotic equilibrium, the solvent which crosses the membrane 15 in a first direction tends to force the working body 11 in a second, opposite direction, whereby the relative volume of the target cavity increases.

Accordingly, reciprocation of working body 11 and thus actuatable members 100A, 100B is achieved by, for example, cyclically changing the direction of osmotic flow across the semi-permeable membrane 15. Since they are all generally connected, the working body 11, actuatable member 100A, and actuatable member 100B generally travel in unison in response to the osmotic influences.

Figure 6:
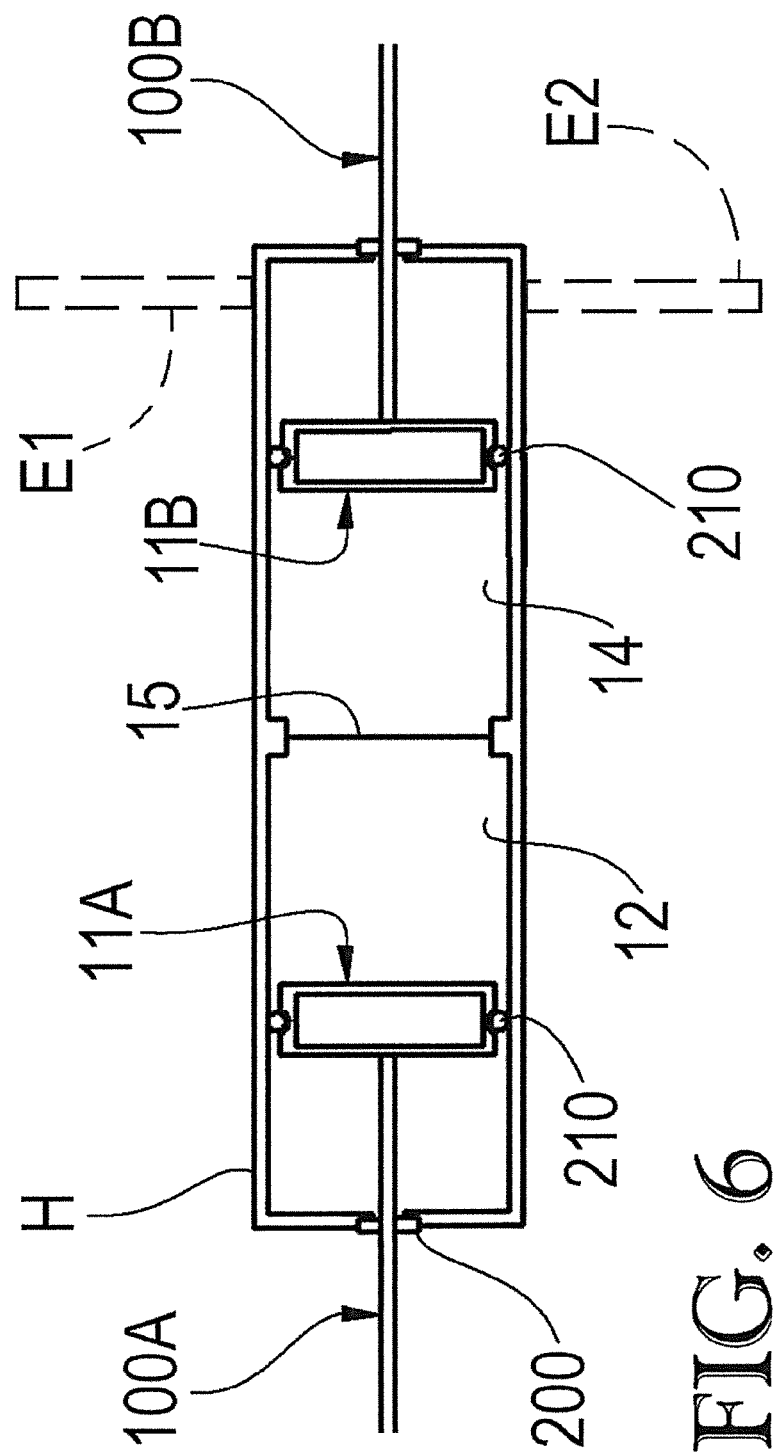
FIG. 6 shows a third embodiment of osmotic energy transfer devices of the invention with the actuatable member(s) in a resting state.
Figure 7A:
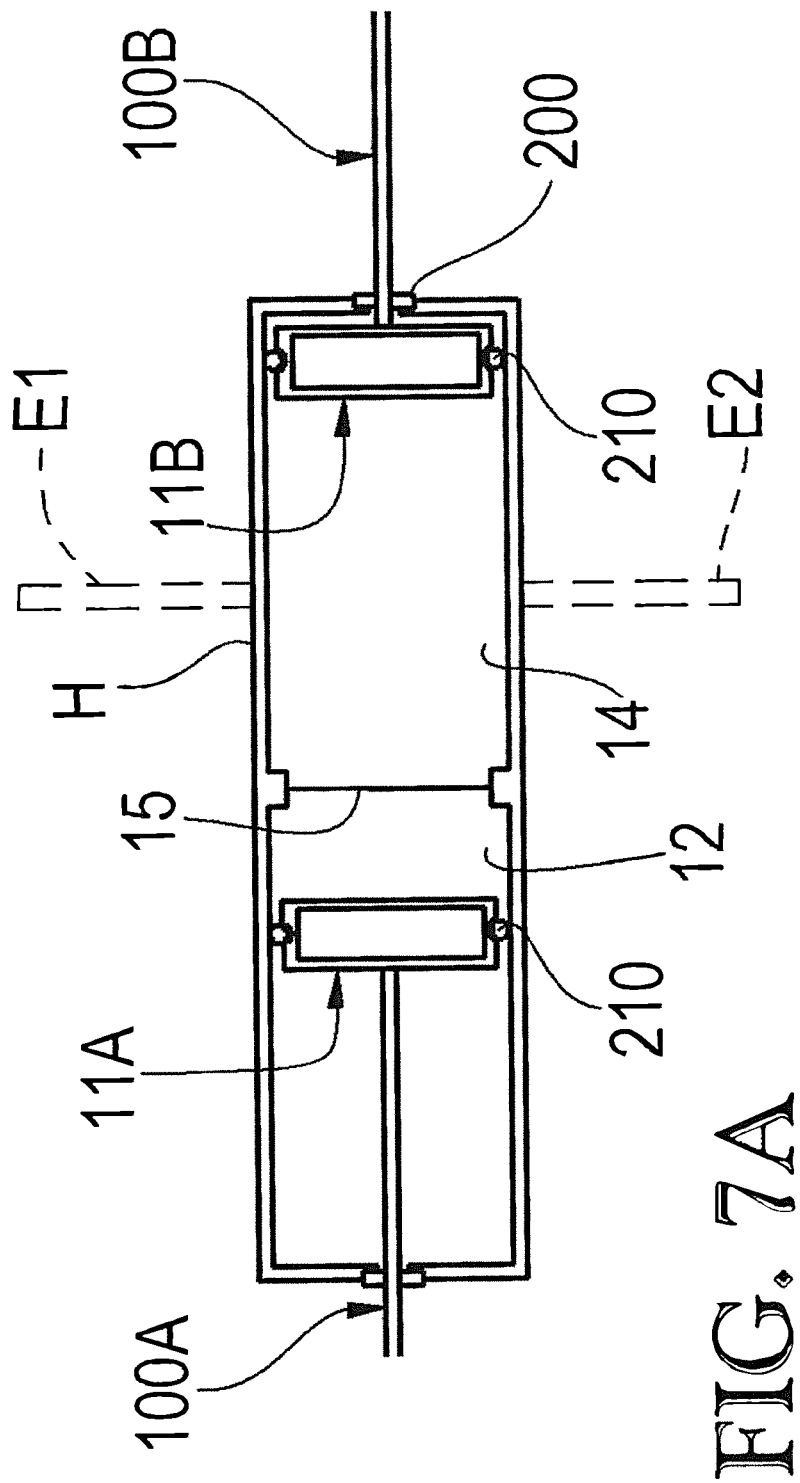
FIG. 7A shows cross sectional view of the osmotic energy transfer device of FIG. 6 with the working bodies in first osmotically urged positions, respectively.

Referring now to FIGS. 6, 7A, and 78, in some embodiments actuatable member 100A and actuatable member 100B general travel in unison, whilst the semi-permeable membrane 15 remains in a generally fixed position.

Figure 7B:
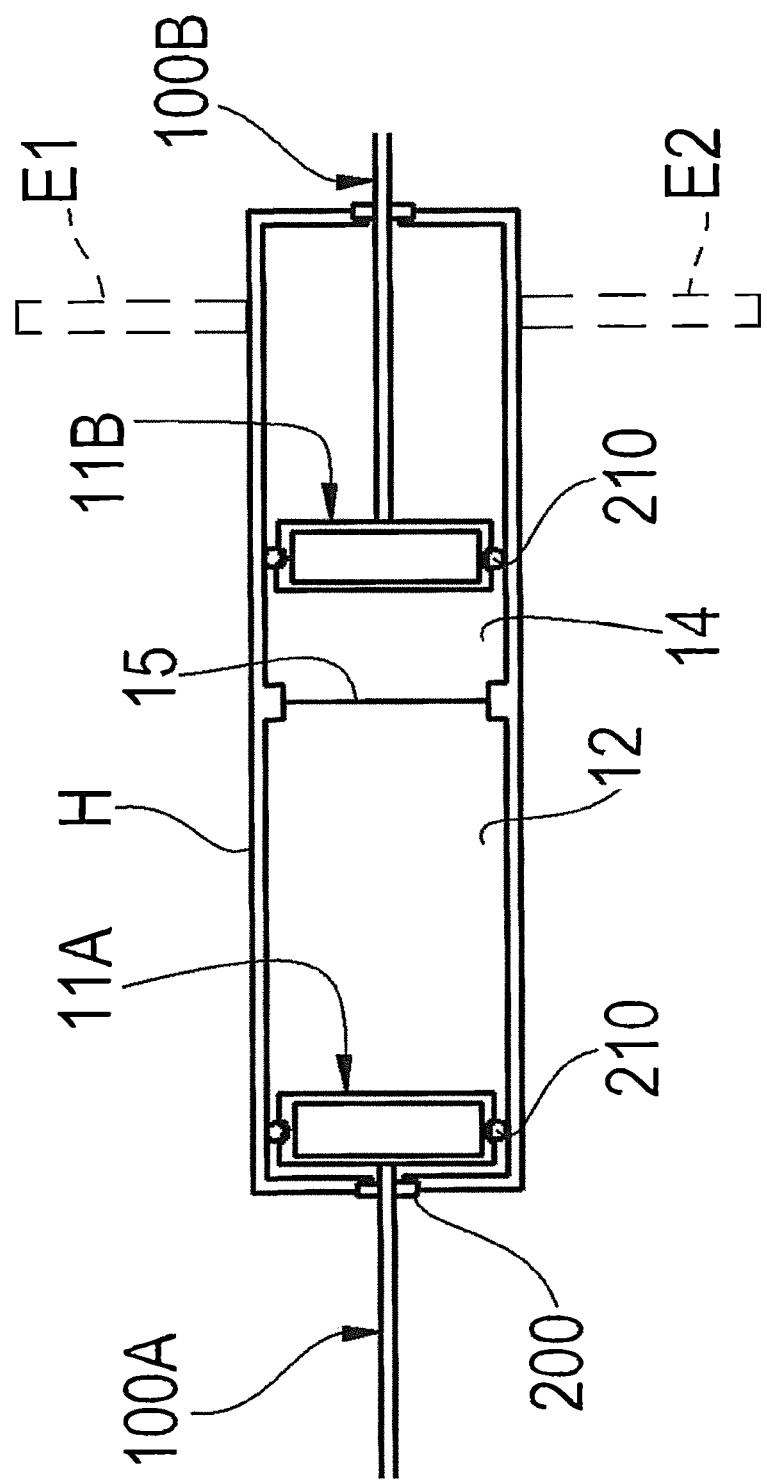
FIG. 7B shows cross sectional view of the osmotic energy transfer device of FIG. 6 with the working bodies second osmotically urged positions, respectively.

Such embodiments include first and second working bodies, namely working bodies 11A and 11B. Similar to working body 11 (FIGS. 3, 4A, 4B, and 5), each working body 11A and 11B of FIGS. 6, 7A, and 7B is sized, adapted, and configured to correspond with the opening dimensions of housing "H", whereby each working body 11A, 11B fits slidably within the housing "H".

The working bodies 11A, 11B are substantially impermeable to the contents of cavities 12 and 14, respectively. In addition, the working bodies 11A, 11B, each further includes rings 210 which are sized, adapted, and configured, to enable generally freely sliding communication between the working body 11A, 11B and housing "H" whilst sufficiently providing a seal between the body 11 and housing "H". Namely, the entire assemblage of working bodies 11A and 11B enable reciprocal movement of actuatable members 100A, 100B, while suitably maintaining a fluid tight seal between the bodies 11A and 11B and housing "H", whereby the contents of cavities 12 and 14 are generally retained therein.

Similar to the other described embodiments, in response to the dynamic changes in the amount of chemically available solute in the separate cavities 12, 14, the system osmotically seeks a state of equilibrium. Again, the solvent flows across the membrane 15 until the opposing forces, on opposing sides of the membrane, generally equalize and the solvent flow ceases.

At this point, one of the cavities 12, 14, has a relatively greater volume whist the other has a relatively lesser volume. A relative reduction in cavity volume corresponds to an inward stroke of the respective actuatable member 100A, 100B, toward the medial portion of the device 8. Correspondingly, a relative increase in cavity volume corresponds to an outward stroke of the respective actuatable member 100A, 100B, away from the medial portion of the device 8.

Referring again to all the FIGURES, using the device requires relatively little end user input. Most of the operation in system 5 is generally managed by the electronic controller "EC."

The following is merely exemplary of one possible method of electronic control. Those skilled in the art are well aware of other suitable electrical-based controlling techniques and corresponding hardware which utilize principles of e.g. electrohydrodynamics, electro-fluid-dynamics, electrokinetics, and electro-osmosis, to create fluid flow occurrences across a membrane.

As one example, the device is energized when controller sends a preferably pulsed DC signal to electrodes "E1" and "E2" each of which are in electrical communication with cavity 14. Namely, when energized, electrode "E1" defines a positive polarity and electrode "E2" defines a negative polarity. The electrodes charge the outer working body 10 to capture the electrolyte ions or stop charging the working body 10 to release the electrolyte ions.

More specifically, each of cavities 12 and 14 contains both a liquid solvent and solute constituents. However, the contents of cavity 14 is a generally electrically conductive electrolyte solution. Correspondingly, since the electrodes "E1" and "E2" communicate with cavity 14, when the electrodes "E1", "E2" are energized, the cations of the electrolyte are electromagnetically drawn to the negative polarity electrode "E2" and the anions of the electrolyte are electromagnetically drawn to the positive polarity electrode "E1".

Since the charged anions and cations accumulate on the electrode "E1", "E2" surfaces, respectively, they are relatively less chemically available to e.g. the solvent constituent of the electrolyte solution. After sufficient exposure to the DC signal and thus after a sufficient amount of ion accumulation on the electrodes "E1", "E2" in cavity 14, the concentration of available solute is relatively greater in cavity 12 than in cavity 14. At that point, an osmotic gradient is defined across the semi-permeable membrane 15.

The system then seeks equilibrium, whereby solvent from cavity 14 flows across semi-permeable membrane 15 and into cavity 12, increasing its relative volume and displacing ones of the actuatable members 100A, 100B in a first direction (FIGS. 2A, 2B, 2C, 4A, 7A).

Next, the DC signal is removed or otherwise mitigated and correspondingly the electrodes "E1", "E2" are de-energized. At this point, the ions lose their affinity for the electrodes and disassociate therefrom, returning to a chemically available state within the electrolyte solution.

Once the electrolyte ions are again chemically available within the solution of cavity 14, the relative solute concentration is greater within cavity 14 than in cavity 12. Correspondingly, the osmotic device 8 defines an osmotic tendency which is generally the opposition direction as compared to when the device was energized. In other words, the resting-condition solute concentrations force a flow of solvent from cavity 12, through semi-permeable membrane 15, and into cavity 14. Thence, the actuatable members 100A, 100B are displaced in generally the opposition direction as compared to when the device 8 was energized (FIGS. 1A, 1B, 1C, 4B, 7B).

The energizing and de-energizing is repeated in a cyclic or pulsed fashion, over time. Thus, the actuatable members 100A, 100B are generally linearly displaced in a reciprocal fashion, with a frequency that corresponds to the frequency of the electrical signal cycle or pulse frequency.

Preferably, various components of the osmotic energy transfer system 5 are made of materials which resist corrosion, and are suitably strong and durable for normal extended use. Those skilled in the art are well aware of certain metallic and non-metallic materials which possess such desirable qualities, and appropriate methods of forming such materials.

Appropriate metallic materials for components of osmotic energy transfer system 5 include, but are not limited to, aluminum, steel, stainless steel, titanium, magnesium, brass, and their respective alloys. Common industry methods of forming such metallic materials include casting, forging, shearing, bending, machining, riveting, welding, powdered metal processing, extruding and others.

Non-metallic materials suitable for components of osmotic energy transfer system 5 are various polymeric compounds, such as for example and without limitation, various of the polyolefins, such as a variety of the polyethylenes, e.g. high density polyethylene, or polypropylenes. There can also be mentioned as examples such polymers as polyvinyl chloride and chlorinated polyvinyl chloride copolymers, various of the polyamides, polycarbonates, and others.

For any polymeric material employed in structures of the invention, any conventional additive package can be included such as, for example and without limitation, slip agents, anti-block agents, release agents, anti-oxidants, fillers, and plasticizers, to control e.g. processing of the polymeric material as well as to stabilize and/or otherwise control the properties of the finished processed product, also to control hardness, bending resistance, and the like.

Common industry methods of forming such polymeric compounds will suffice to form non-metallic components of osmotic energy transfer system 5. Exemplary, but not limiting, of such processes are the various commonly-known plastics converting processes.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

I claim:

1. A method of converting energy of an osmotic system into a different form of energy, the method comprising:
   (a) providing a working body which defines an enclosure having a fluid filled cavity therein and having a semi-permeable membrane housed in the cavity which generally divides the cavity into first and second chambers, wherein the fluid filled cavity contains a solvent fluid having a solute contained therein, wherein the solvent fluid and the solute comprise an electrically conductive electrolyte solution;
   (b) introducing an electric field to the working body and correspondingly driving an osmotic response across the semi-permeable membrane in a first direction of fluid transfer and converting forces associated with such fluid transfer into mechanical movement of an actuatable member in a corresponding first direction of movement, wherein the electric field changes a concentration of the solute within the solvent fluid within one of the first and second chambers, wherein the electric field is introduced by activating a first electrode and a second electrode, the first electrode and the second electrode being in electrical communication with the fluid filled cavity, and wherein when the first electrode and the second electrode are activated, cations and anions in the electrically conductive electrolyte solution are drawn to the first electrode and the second electrode, respectively;
   (c) manipulating the electric field so as to drive an osmotic response across the semi-permeable membrane in a second, opposite, direction of fluid transfer and converting forces associated with such fluid transfer into mechanical movement of the actuatable member in a corresponding second, opposite, direction of movement, wherein the fluid transfer includes transferring the solvent fluid from the one of the first and second chambers with the relatively lesser concentration of solute, across the semi-permeable membrane, into the other one of the first and second chambers with the relatively greater concentration of solute,
      wherein the osmotic response across the semi-permeable membrane in the first direction occurs after the first electrode and the second electrode have been activated for a sufficient amount of time, causing a concentration of the solute to be greater in the other one of the first and second chambers; wherein the solvent fluid flows from the one of the first and second chambers into the other one of the first and second chambers after the first electrode and the second electrode have been activated for the sufficient time, increasing a relative volume of the electrically conductive electrolyte solution in the other one of the first and second chambers and displacing the actuatable member; and wherein the osmotic response across the semi-permeable membrane in the second, opposite, direction occurs after the first electrode and the second electrode have been de-energized for a sufficient time and a concentration of the solute is greater in the one of the first and second chambers; and
   (d) repeatedly manipulating the electric field such that the actuatable member cycles between first and second positions which respectively correspond to the first and second directions of movement.

2. The method of converting energy of claim 1, further comprising establishing the electric field by providing a direct current (DC) signal.

3. The method of converting energy of claim 1 wherein the actuatable member moves along a generally linear travel path.

4. The method of converting energy of claim 1 further comprising converting the movement of the actuatable member into a rotational movement.

5. The method of converting energy of claim 1, further comprising providing a piston which lies between the working body and the actuatable member.

6. The method of converting energy of claim 1, further comprising the step of deforming the working body by generally axially stretching the working body.

7. The method of converting energy of claim 1, further comprising the step of deforming the working body by generally axially compressing the working body.

8. The method of converting energy of claim 1 wherein the first and second positions correspond to a maximum distance traveled by the actuatable member in the first and second directions, respectively.

9. The method of converting energy of claim 1, wherein the solvent fluid flows from the second chamber into the first chamber after the first electrode and the second electrode have been de-energized for the sufficient time, increasing a relative volume of the electrically conductive electrolyte solution in the first chamber and displacing the actuatable member.

* * * * *